United States Patent
Perng et al.

(10) Patent No.: US 7,104,127 B2
(45) Date of Patent: Sep. 12, 2006

(54) NONDESTRUCTIVE METHOD FOR INSPECTING CLADDING TUBES

(75) Inventors: Kang-Neng Perng, Sanyi Shiang (TW); Ching-Shih Liu, Longtan Shiang (TW)

(73) Assignee: Institute of Nuclear Energy Research Atomic Energy Council, Executive Yuan, Taoyuan (TW)

(*) Notice: Subject to any disclaimer, the term of this patent is extended or adjusted under 35 U.S.C. 154(b) by 68 days.

(21) Appl. No.: 11/058,159

(22) Filed: Feb. 16, 2005

(65) Prior Publication Data

US 2006/0062343 A1   Mar. 23, 2006

(30) Foreign Application Priority Data

Sep. 17, 2004   (TW) ............................... 93128124 A

(51) Int. Cl.
| | |
|---|---|
| *G01F 23/28* | (2006.01) |
| *G01F 23/296* | (2006.01) |
| *G01N 21/88* | (2006.01) |
| *G01F 23/284* | (2006.01) |
| *G01F 23/292* | (2006.01) |
| *G21C 17/017* | (2006.01) |

(52) U.S. Cl. .................... 73/290 V; 376/251; 376/252; 250/900; 250/901; 250/559.45; 250/559.46

(58) Field of Classification Search .............. 73/290 V, 73/622
See application file for complete search history.

(56) References Cited

U.S. PATENT DOCUMENTS

| 4,065,960 | A | * | 1/1978 | Grabendorfer et al. | ........ 73/609 |
| 4,320,659 | A | * | 3/1982 | Lynnworth et al. | ........... 73/589 |
| 4,630,476 | A | * | 12/1986 | Moore | ......................... 73/293 |
| 4,679,430 | A | * | 7/1987 | Scott-Kestin et al. | ..... 73/290 V |
| 4,735,097 | A | * | 4/1988 | Lynnworth | ............... 73/861.28 |
| 5,015,995 | A | * | 5/1991 | Holroyd | ..................... 340/621 |
| 6,367,328 | B1 | * | 4/2002 | Gorman et al. | ............... 73/592 |

* cited by examiner

*Primary Examiner*—Hezron Williams
*Assistant Examiner*—Rose M. Miller
(74) *Attorney, Agent, or Firm*—Troxell Law Office PLLC

(57) ABSTRACT

The present invention relates to a nondestructive method or inspecting defects of the cladding of a nuclear fuel rod, which is featured by a wave emitter obliquely discharging an inspection wave to an inspected tube and a receiver arranged at a side of the inspected tube with respect to the wave emitter. If liquid is accumulated inside the tube, the incident inspection wave will be refracted so that the receiver can receive the refracted inspection wave at a specific location. The method can determine whether liquid is accumulated inside the tube and further is able to detect the level of the liquid.

11 Claims, 2 Drawing Sheets

NONDESTRUCTIVE METHOD FOR INSPECTING CLADDING TUBES

FIELD OF THE INVENTION

The present invention relates to a method for inspecting defects of the cladding of a nuclear fuel rod, and more particularly, to a nondestructive method for measuring internal liquid level and detecting leakages of a cladding tube. To be more specific, the method of the invention provides a wave obliquely incident to a tube at a specified incident position for checking whether a liquid exists inside the tube at the incident position by detecting the wave received at the side of the tube opposite to the incident position.

BACKGROUND OF THE INVENTION

Since the fuel rod placed in the reactor core of a light water nuclear reactor is compromised of a Zircaloy cladding tube filled with uranium fuel pellets, once the cladding breaks, the nuclear fuel therein could be released into the reactor as to radioactively pollute the cooling water that, as a consequence, the safety of the whole nuclear power plant is affected and the radioactivity of the material discharged therefrom is increased. In a worse scenario, the operation of the nuclear power plant will have to be shut down for inspection so that causes a severe economic loss. In this regard, a method capable of detecting precisely the defects of a cladding tube can play an important role for preventing the above-mentioned economic loss by avoiding the foregoing radioactive pollution from happening. However, it is not an easy and convenient job for even a trained technician to identify a defect using the current ultrasonic inspection method that is usually the cause of detainment for a scheduled maintenance of nuclear power plant. Therefore, an improve inspection method, which is fast and precise, can save the maintenance cost in millions by the saving of working hours for the maintenance. It is one of the most important safety features for a nuclear power plant to be able to rapidly and precisely detect a fuel rod with defected cladding so as to proceed with the replacement of the defected fuel rod.

Refer to FIG. 1A and FIG. 1B, which are schematic illustrations showing a conventional ultrasonic inspection method used by most nuclear power plant for detecting defects of a fuel rod. As seen in FIG. 1A, an ultrasonic signal 111 emitted from an ultrasonic emitter 11 is vertically-incident to the cladding tube 12 of a fuel rod to be inspected that the ultrasonic signal 111 will travel through the internal 121 of the tube and finally to be received by the receiver 13. The magnitude of the ultrasonic signal 111 received by the receiver 13 will increase when there is cooling water accumulated in the internal 121 of the tube caused by a cracking of the cladding 12 enabling the cooling water to enter therefrom. By which, the situation of water accumulated inside a cladding tube can be detected.

FIG. 1B shows another method for detecting the situation of water accumulated inside a cladding tube. Similarly, an ultrasonic signal 111 emitted from an ultrasonic emitter 11 is vertically incident to the cladding tube 12 of a fuel rod and further into the internal 121 of the tube. If there exists the situation of water accumulated inside a cladding tube caused by the cracked cladding tube 12, the ultrasonic signal 111 traveling inside the tube will be attenuated and reflected and the reflected signal will be received by the receiver 11'. That is, if an attenuated ultrasonic signal is detected by the receiver 11', there is surely water accumulated inside the cladding tube.

From the above description, the conventional inspection method has the following shortcomings:

(1) The reliability of the conventional inspection method is low, since a minute decrease of signal might not be caused by accumulated water resulting from defected cladding. Moreover, it is difficult to identify a variation in magnitude of the ultrasonic signal, since noise will have an effect while evaluating the magnitude of the signal.
(2) The convention inspection method can only determine whether there is water accumulated inside the cladding tube, but can not detect the exact position of cracking or defect.
(3) The inspection accuracy of the convention inspection method is easily affected by the shape of the object to be inspected. It is more suitable to be used for inspecting a flat object and not for a hollow tube or an object with curved surface.
(4) The convention inspection method is substantially a method of two-dimensional measuring, which is not as effective while it is used for inspecting defects of an upright cladding tube.

Thus, it is indeed a pressing requirement for improving the conventional inspection method.

SUMMARY OF THE INVENTION

It is the primary object of the invention to provide a nondestructive method for inspecting defects of the cladding of a nuclear fuel rod, in which an inspection wave is obliquely incident to the cladding tube for checking whether water is accumulated inside the cladding tube by utilizing the refraction phenomenon of the inspection wave while the same traveling between different mediums.

It is another object of the invention to provide a nondestructive method for inspecting defects of the cladding of a nuclear fuel rod, which is capable of detecting the liquid level inside the cladding tube by providing an inspection wave obliquely incident to the cladding tube so as to utilize the refraction phenomenon of the inspection wave while the same traveling between different mediums.

To achieve the above objects, the nondestructive method for inspecting defects of the cladding of a nuclear fuel rod of the present invention comprises the steps of:

(a) providing a tube to be inspected, wherein the tube comprises an outer surface and an internal surface;
(b) arranging a wave emitter close to a side of the tube to be inspected for discharging an inspection wave obliquely incident to a first position on the outer surface by a predefined tilt angle and subsequently progressing to come into contact with the internal surface at a second position thereon;
(c) arranging a receiver at another side of the tube with respect to the wave emitter for receiving the inspection wave passing through the tube;
(d) making an evaluation to determine whether the passing-through inspection wave can only be detected by the receiver while the same is being arranged at a specific position at another side of the tube with respect to the wave emitter; if so, it represents that there is no liquid existed inside the tube under the level indicated by the second position;

(e) making an evaluation to determine whether the passing-through inspection wave can be detected by the receiver while the same is being arranged at two different positions both at another side of the tube with respect to the wave emitter; if so, it represents that there is liquid existed inside the tube at the level indicated by the second position.

Other and further features, advantages and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

DESCRIPTION OF THE PREFERRED EMBODIMENT

For your esteemed members of reviewing committee to further understand and recognize the fulfilled functions and structural characteristics of the invention, several preferable embodiments cooperating with detailed description are presented as follows.

Figures 1A, 1B:
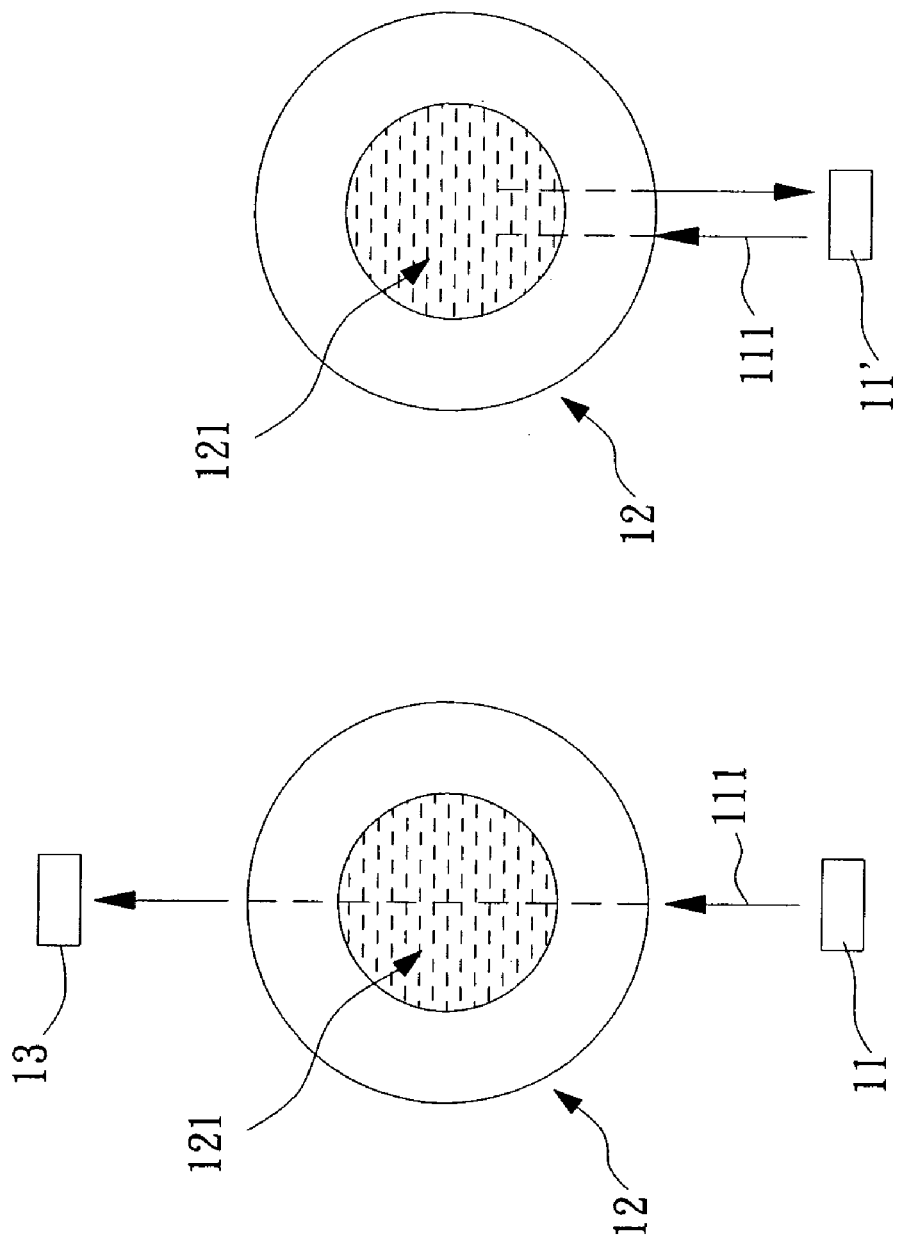
FIG. 1A and FIG. 1B are schematic illustrations showing a conventional method using ultrasonic wave for inspecting defects of the cladding of a fuel rod.
Figure 2B:
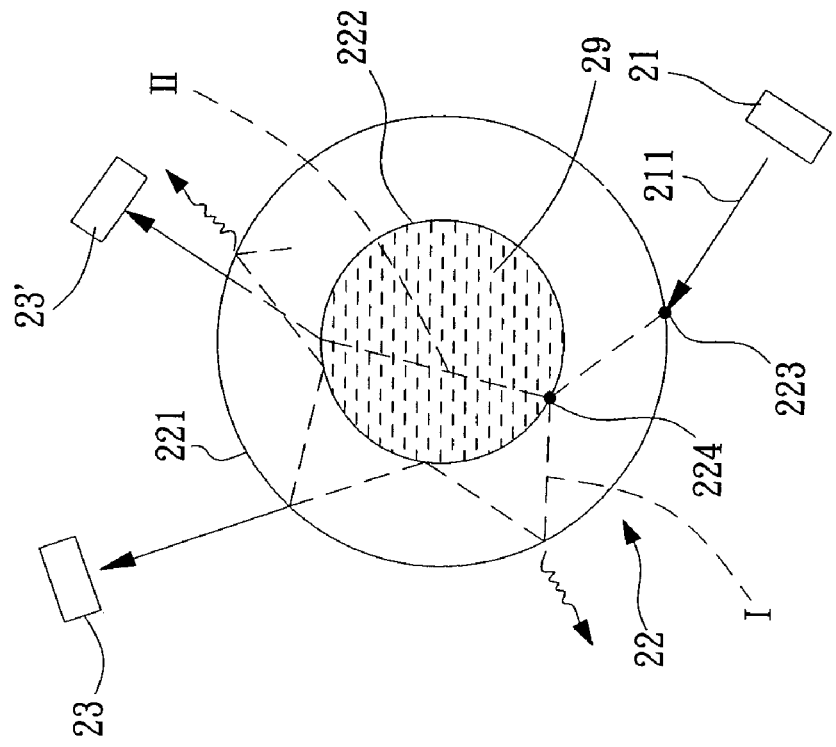
FIG. 2B is a schematic illustration of using a nondestructive method of the present invention to inspect the cladding of a nuclear fuel rod while there is liquid accumulated inside the cladding.
Figure 2A:
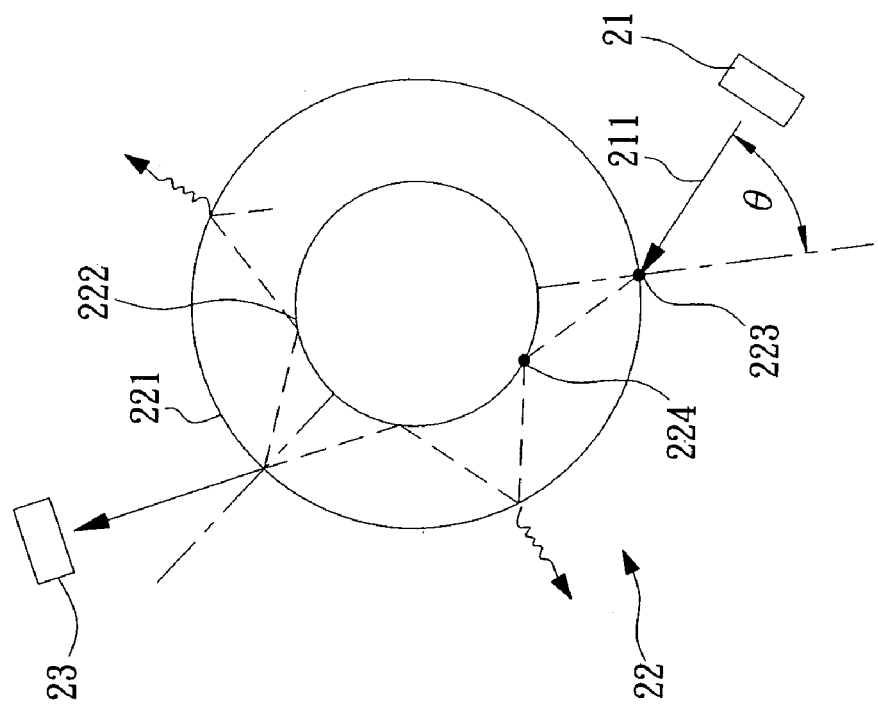
FIG. 2A is a schematic illustration of using a nondestructive method of the present invention to inspect the cladding of a nuclear fuel rod while there is no liquid accumulated inside the cladding.

Please refer to FIG. 2A, which is a schematic illustration of using a nondestructive method of the present invention to inspect the cladding tube 22 of a nuclear fuel rod while there is no liquid accumulated inside the cladding tube 22. As seen in FIG. 2A, a tube 22 to be inspected having an outer surface 221 and an internal surface 222 is provided where a wave emitter 21 is arranged close to a side of the tube 22 for obliquely discharging an inspection wave 211. In a preferred embodiment of the invention, the inspection wave 211 is substantially an ultrasonic wave. After discharging, the inspection wave 211 will be incident to a first position 223 on the outer surface 221 by a predefined tilt angle θ and subsequently progressing to come into contact with the internal surface 222 at a second position 224 thereon. Since the frequency of the ultrasonic wave is ranged between 1 MHz and 25 MHz which is very high and can only be transmitted through a medium. While there is no cracking on the tube and thus no liquid accumulated inside the tube, there will be hardly any medium existed in the tube capable of transmitting the ultrasonic wave used as the inspection wave 211 and thus most of the inspection wave 211 will be reflected while coming into contact with the second position 224 on the internal surface 222 without passing through the same and entering into the tube 22. As a consequence, the inspection wave 211 will progress along the path shown as the dotted line of FIG. 2A and finally out of the tube 22 at a proper position to be received by the receiver 23 arranged at another side of the tube 22 with respect to the wave emitter 21.

It is noted that the transmission mechanism defining the path of the inspection wave 211 is very complicated while the same is progressing inside the wall of the tube 22 between the outer surface 221 and the internal surface 222, that the path is highly related to the material of the tube 22 and the incident angle of the inspection wave 211. However, there is still a portion of the inspection wave dissipating out of the tube wall during each reflection as shown by the twist arrows of FIG. 2A. As a matter of fact, the wave received by the receiver 23 is only the signal of the reflected inspection wave with highest intensity that is not exactly the whole original inspection wave 211.

Please refer to FIG. 2B, which is a schematic illustration of using a nondestructive method of the present invention to inspect the cladding of a nuclear fuel rod while there is liquid accumulated inside the cladding. Similarly, a tube 22 to be inspected having an outer surface 221 and an internal surface 222 is provided where a wave emitter 21 is arranged close to a side of the tube 22 for obliquely discharging an inspection wave 211. In a preferred embodiment of the invention, the inspection wave 211 is substantially an ultrasonic wave. After discharging, the inspection wave 211 will be incident to a first position 223 on the outer surface 221 by a predefined tilt angle θ and subsequently progressing to come into contact with the internal surface 222 at a second position 224 thereon. Since a liquid 29 is already existed inside the tube 22 that is not the same material as the one of the tube 22, the second position 224 is acted as an interface formed between the liquid and the material of the tube while the inspection wave 211 progresses to the second position 224. In this regard, at the second position 224, a portion of the ultrasonic wave used as the inspection wave 211 is reflected and progresses along a reflection path, i.e. the first path, as the one shown in the dotted line I of FIG. 2B which is finally being transmitted out of the tube 22 at a proper position to be received by the first receiver 23 arranged at another side of the tube 22 with respect to the wave emitter 21. In addition, according to Snell's law of refraction, some other portion of the ultrasonic wave used as the inspection wave 211 is refracted at the second position and enters into the liquid 29 following the path shown in the dotted line II of FIG. 2B which is further refracted by the interface between the liquid and the material of tube 22 so as to be transmitted out of the tube 22 and is received by the second receiver 23'.

In retrospect to the above description, if two different passing-through inspection waves 211 respectively can be detected by two receivers 23, 23' while the same are respectively being arranged at two different positions both at another side of the tube 22 with respect to the wave emitter 21, it represents that there is liquid existed inside the tube. Similarly, there is still a portion of the inspection wave 211 dissipating out of the tube wall during each reflection as shown by the twist arrows of FIG. 2B. As a matter of fact, the wave received by the first receiver 23 is only the signal of the reflected inspection wave with highest intensity that is not exactly the whole original inspection wave 211. In addition, the total intensity of the signal received by the first receiver 23 and the second receiver 23' is smaller than the original inspection wave 211. Moreover, the signal intensity of the wave received by the first receiver 23 while there is liquid accumulated inside the tube 22 is obviously smaller than that of the wave received by the first receiver 23 while there is no liquid existed in the tube 22, and the signal intensity of wave received by the second receiver 23' of FIG. 2B is also larger than that of the wave received by the first receiver 23.

Moreover, the path of the inspection wave 211 transmitting between the internal surface 222 and outer surface 221 of the tube 22 and the refraction angle defining the refraction of the inspection wave 211 while the same entering the liquid 29 are closely related to the material made of the tube 22, the incident angle θ and the refraction index of the liquid 29. Hence, an elaborate calculation procedure is required for obtaining a precise incident angle for the inspection wave while using the conventional method for inspecting a cladding tube. On the other hand, the method of the present invention is capable of achieving the disclosed inspection object without requiring ascertained parameters. That is, as soon as two obvious signals are detected at a side of the inspected tube with respect to the wave emitter, it can be certain that there is liquid existed in the tube.

In another preferred embodiment of the invention, the wave emitter 21 can be connected to a driving mechanism (not shown in the figures), which can drive and position the wave emitter 21 at different locations allowable by the current setting for enabling the wave emitter 21 to discharge inspection wave to the inspected tube by different incident angle. In addition, the first receiver 23 and the second receiver 23' of FIG. 2B can be integrated into a signal receiving device, which is similarly being connected to a driving mechanism for enabling the receiving device to search the inspection wave actively. Yet, in another embodiment of the invention, the receiving device is stationary, but is arranged with a specified amount of receivers therein, which is also capable of achieving the same effect as the active receiving device.

The embodiments described above are all related to a method for inspecting a tube, and more particular, to a method for detecting leakages of a waterproof tube. However, the method of the invention can further be employed by the industry for detecting liquid level of a storage tank storing corrosive liquid or liquid pollutant. In this regard, the wave emitter is driven and positioned by a driving mechanism enabling the emitter to discharge wave to an inspected object at different altitudes while an evaluation is being made for determine whether there is liquid existed at those altitudes according to the amount of signals received by the receiver. Hence, the present invention can be implemented for detecting the level of liquid accumulated in an upright tubular object.

Yet, in another preferred embodiment of the invention, light wave can be employed as the inspection wave while the tube 22 is made of a transparent material. The operation of the present embodiment of using light wave as the inspection wave is similar to that of the prior embodiment that is not described further hereinafter. However, the present embodiment of using light wave enables the method of the invention to be adopted massively by the unmanned monitoring apparatus of an automation production system.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A nondestructive method for determining a defective cladding of a nuclear fuel rod from the presence of a liquid in the fuel rod, comprising the steps of:
   (a) providing a tube to be inspected, wherein the tube comprises an outer surface and an internal surface;
   (b) arranging a wave emitter close to a side of the tube to be inspected for discharging an inspection wave obliquely incident to a first position on the outer surface by a predefined tilt angle and subsequently progressing to come into contact with the internal surface at a second position thereon;
   (c) arranging a receiving device at another side of the tube with respect to the wave emitter for receiving the inspection wave passing through the tube;
   (d) making an evaluation to determine whether the passing-through inspection wave can only be detected by the receiving device while the same is being arranged at a specific position at another side of the tube with respect to the wave emitter; if so, it represents that there is no liquid existed inside the tube under the level indicated by the second position;
   (e) making an evaluation to determine whether the passing-through inspection wave can be detected by the receiving device while the same is being arranged at two different positions both at another side of the tube with respect to the wave emitter; if so, it represents that there is liquid existed inside the tube at the level indicated by the second position.

2. The method as recited in claim 1, wherein the wave emitter is connected to a driving mechanism for driving the wave emitter to move up and down along the tube.

3. The method as recited in claim 2, wherein the level of liquid accumulated in the tube is detected by moving the wave emitter up and down along the tube while repeating the step (b) to step (e).

4. The method as recited in claim 1, wherein the tube is substantially a Zircaloy cladding tube.

5. The method as recited in claim 1, wherein the inspection wave is substantially an ultrasonic wave.

6. The method as recited in claim 1, wherein the inspection wave is substantially a light wave.

7. The method as recited in claim 6, wherein the tube is made of a transparent material.

8. The method as recited in claim 1, wherein the receiving device comprises at least a receiver.

9. The method as recited in claim 8, wherein the receiving device can be moved up-and-down and back-and-forth the tube for receiving the inspection waves discharging from different positions of the outer surface of the tube.

10. The method as recited in claim 1, wherein the receiving device comprises a plurality of receivers.

11. The method as recited in claim 1, wherein the receiving device is substantially a stationary device capable of receiving the inspection waves discharging from different positions of the outer surface of the tube by a plurality of receivers disposed at different areas of the receiving device.

* * * * *